United States Patent [19]

Butz et al.

[11] Patent Number: 5,272,083

[45] Date of Patent: * Dec. 21, 1993

[54] CULTURE DEVICE AND METHOD OF USE HAVING A DETACHABLE CELL OR TISSUE GROWTH SURFACE

[75] Inventors: David Butz, Westford, Mass.; George Lyman, Cape Porpose, Me.; David Root, Lexington; Gregory Mathus, Concord, both of Mass.

[73] Assignee: Costar Corporation, Cambridge, Mass.

[*] Notice: The portion of the term of this patent subsequent to Aug. 18, 2009 has been disclaimed.

[21] Appl. No.: 705,767

[22] Filed: May 28, 1991

Related U.S. Application Data

[63] Continuation-in-part of Ser. No. 595,305, Oct. 10, 1990, Pat. No. 5,139,951.

[51] Int. Cl.⁵ .......................... C12N 5/06; C12M 3/06
[52] U.S. Cl. .......................... 435/240.241; 435/284; 435/297; 435/311; 422/101; 422/102
[58] Field of Search .............. 435/1, 240.1, 240.241, 435/240.2, 240.23, 284–286, 296–298, 299–301, 310, 311, 313, 315, 316, 809; 422/101, 102; 210/239, 249, 250, 321.84, 348, 460, 463, 470, 471, 473, 476, 482

[56] References Cited

U.S. PATENT DOCUMENTS

| | | | |
|---|---|---|---|
| 2,677,646 | 5/1954 | Lovell et al. | 435/292 |
| 2,761,813 | 9/1956 | Goetz | 435/301 |
| 3,275,528 | 9/1966 | Ainis | 435/284 |
| 4,012,288 | 3/1977 | Lyman et al. | 435/298 |
| 4,106,235 | 8/1978 | Smith | 47/59 |
| 4,125,436 | 11/1978 | Liner | 435/287 |
| 4,246,339 | 1/1981 | Cole et al. | 435/287 |
| 4,308,351 | 12/1981 | Leighton et al. | 435/284 |
| 4,349,632 | 9/1982 | Lyman | 435/284 |
| 4,495,289 | 1/1985 | Lyman et al. | 435/300 |
| 4,603,105 | 7/1986 | Kaplan | 435/297 |
| 4,608,342 | 8/1986 | Nees | 435/297 |
| 4,670,396 | 6/1987 | Bear et al. | 435/287 |
| 4,686,190 | 8/1987 | Cramer et al. | 435/291 |
| 4,871,674 | 10/1989 | Matsui et al. | 435/285 |
| 5,026,649 | 6/1991 | Lyman et al. | 435/284 |
| 5,139,951 | 8/1992 | Butz et al. | 435/284 |

FOREIGN PATENT DOCUMENTS

| | | |
|---|---|---|
| 0239697 | 10/1987 | European Pat. Off. |
| 0242326 | 10/1987 | European Pat. Off. |
| 0261676 | 3/1988 | European Pat. Off. |
| 0334015 | 9/1989 | European Pat. Off. |
| 0408940 | 1/1991 | European Pat. Off. |
| 1003489 | 2/1957 | Fed. Rep. of Germany ......... 47/63 |
| 2563232 | 10/1985 | France ......................... 435/311 |
| 9015862 | 12/1990 | PCT Int'l Appl. |
| 1501563 | 2/1978 | United Kingdom. |

OTHER PUBLICATIONS

ICN Biomedicals, Inc. "Cellagen Membranes", product brochure (Aug. 1987).

Primary Examiner—Jeffrey E. Russel
Assistant Examiner—William H. Beisner
Attorney, Agent, or Firm—Wolf, Greenfield & Sacks

[57] ABSTRACT

A tissue or cell growth device is described for placement within a well of a cluster dish. The device has a cell or tissue retention element detachably attached to a hanger. The hanger preferably has openings allowing access to the well without removal of the member and is capable of positioning the cell or tissue retention element a preselected distance relative to the hanger. Also described are various embodiments of the device having differently shaped hangers and the combination of the device and a cluster dish.

11 Claims, 5 Drawing Sheets

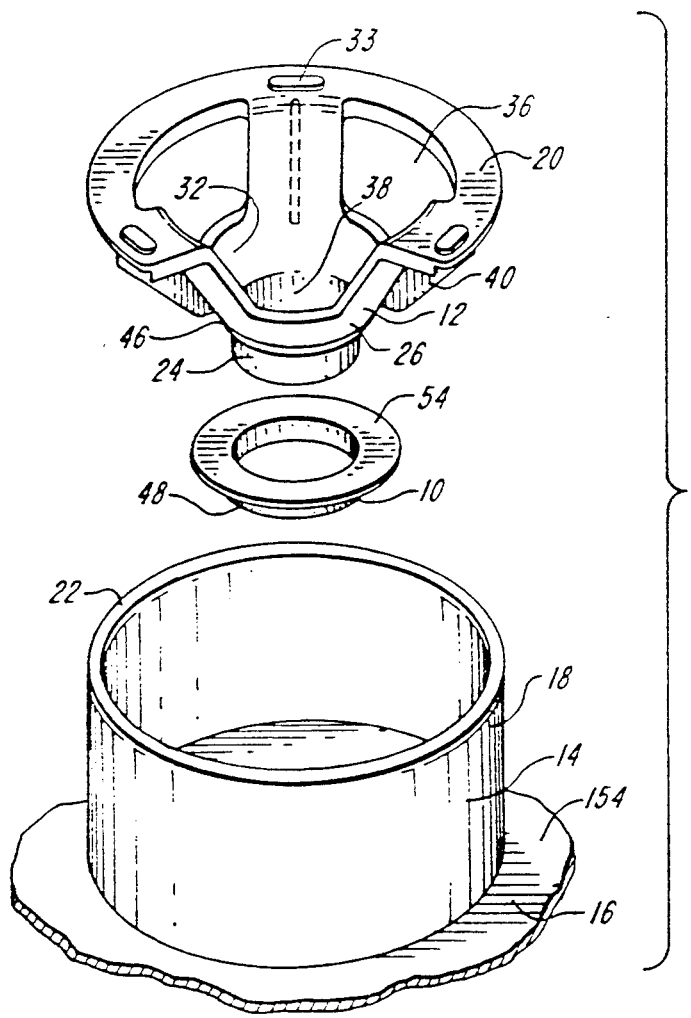
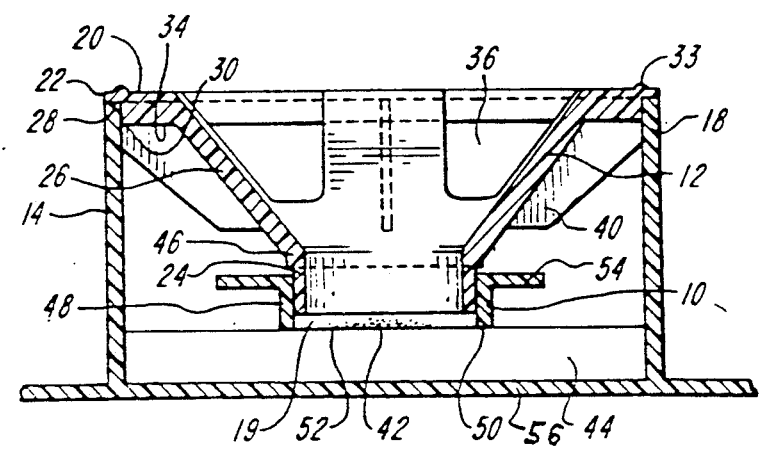
FIG. 1
FIG. 2

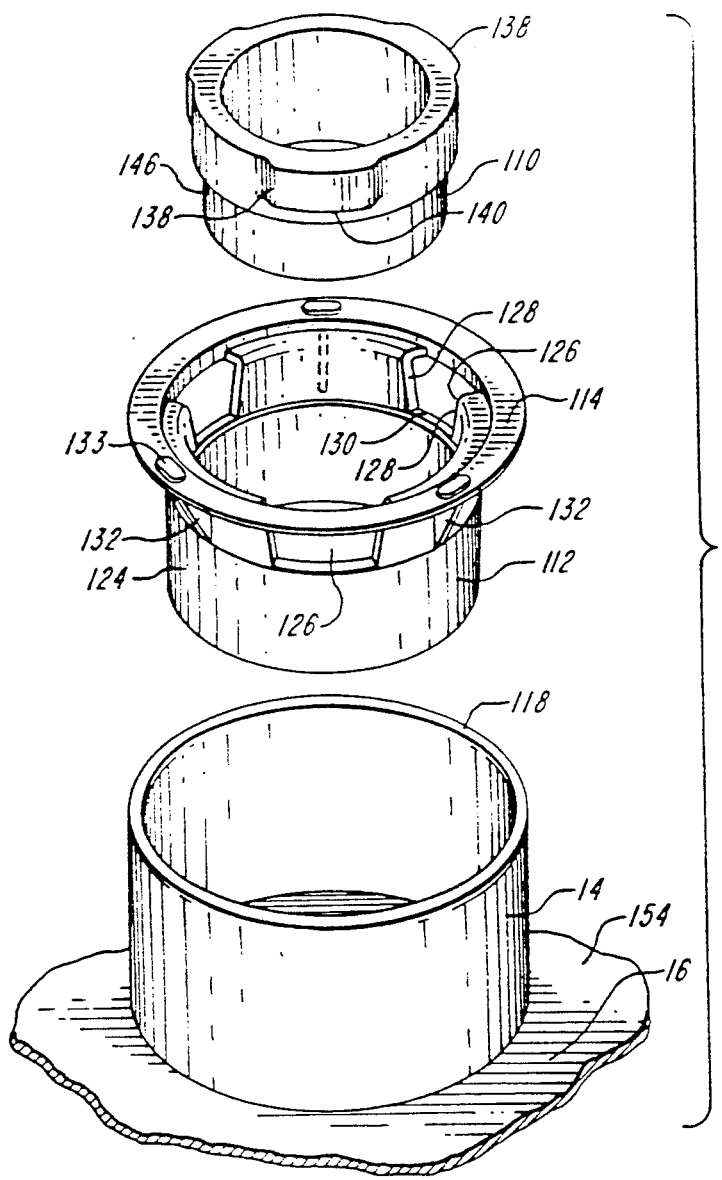
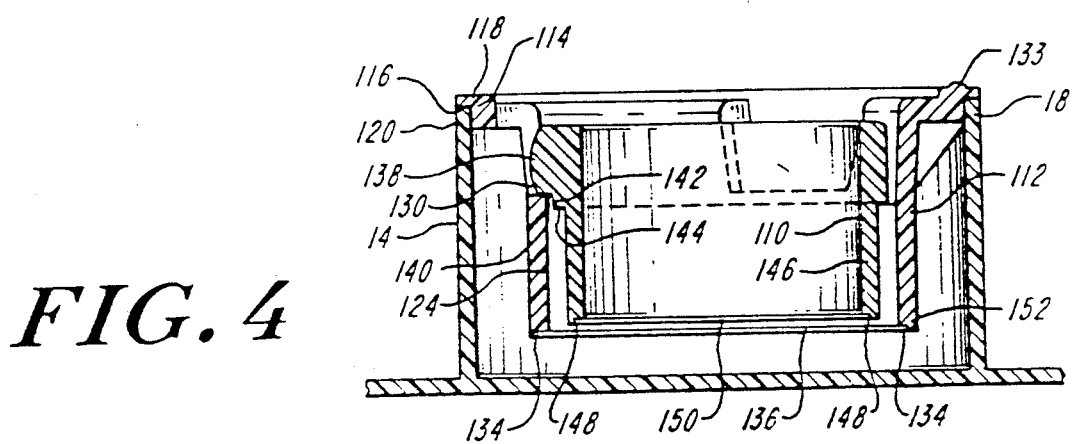

CULTURE DEVICE AND METHOD OF USE HAVING A DETACHABLE CELL OR TISSUE GROWTH SURFACE

RELATED APPLICATION

This application is a continuation-in-part of parent application Ser. No. 07/595,305, filed Oct. 10, 1990, now U.S. Pat. No. 5,139,951, for a A CULTURE DEVICE HAVING A DETACHABLE CELL OR TISSUE GROWTH SURFACE.

FIELD OF THE INVENTION

This invention relates to a device for growing cells or tissues in vitro.

BACKGROUND

In the conventional art of in vitro growth of tissues or cells, biological samples are typically fixed to the bottom of a tube or petri dish and bathed from above with nutrient solution or culture media. This arrangement does not reflect the manner in which the cells receive nutrients in vivo.

An improved tissue culture apparatus, the transwell, is described in applicant's U.S. Pat. No. 5,026,649 issued Jun. 25, 1991, the disclosure of which is incorporated herein by reference. In the Transwell TM, the tissue sample is separated from the nutrient medium by a permeable membrane. A concentration gradient of nutrients then may develop and feed the cells through this permeable membrane, which arrangement more closely reflects to the situation in vivo. The permeable membrane is attached to the bottom end of a tubular support that in turn hangs by a flange at its upper end from the top of a well containing the nutrients. Typically, the well is part of a tissue culture dish. The flange of the support positions the support and membrane centrally in the well. Openings in the side wall of the support provided access for a pipette to add and withdraw fluid from the well.

SUMMARY

The present invention in one aspect is an improved transwell. It is formed of two separable pieces, rather than as a unitary piece as in the transwell. In particular, the portion of the device used to support the growth of cells which typically is a membrane, is detachably secured to the portion of the device used to suspend the membrane within a well containing growth medium. This arrangement affords easy manipulation of the cultured cells.

The two-piece transwell has two components, a cell retention element and a hanger for suspending the cell retention element at a preselected location within a well. The retention element is detachably secured to the bottom portion of the hanger. The cell retention element includes a porous membrane growth surface. The hanger is constructed and arranged such that it may be suspended from the periphery of the well, with a bottom portion of the hanger extending into the well. When the hanger is suspended from the periphery of the well, the retention element is suspended horizontally within the well at a preselected location within the well.

In one embodiment, the retention element is secured to the bottom of the hanger by a friction fit. In another embodiment, the retention element is secured to the bottom of the hanger by a friction fit but in an inverted orientation compared to that of the first embodiment. In yet another embodiment, the retention element is hung from the hanger.

The hanger preferably includes an outwardly extending flange which is stepped so that it may hang upon the upper end of a well in a tissue culture cluster dish. The stepped flange prevents the hanger from shifting laterally within the well, thereby keeping the side wall of the hanger spaced from the side wall of the well so as to prevent capillary action of fluid between the side wall. Capillary action is further prevented in one embodiment by the use of a funnel-shaped hanger which further removes the side wall of the hanger from the side wall of the well. The flange is discontinuous to provide an opening which allows a pipette to be inserted into the space between the hanger and the side wall of the well to provide access to the medium within the well.

Another aspect of the invention is the retention element itself. The retention element preferably has a side wall defining an interior and a peripheral lip extending from the side wall. A membrane is attached to the bottom surface of the side wall forming a tissue or cell growth support. The peripheral lip permits easy manipulation of the retention element, as well as providing structure which permits the use of the retention element in certain flow devices, described in greater detail below.

According to another aspect of the invention, both the retention element and the bottom of the hanger carry porous membranes. In this instance, an assembly is created that provides for two membranes and three media chambers, one below, one between and one above the membranes. This allows cells to be grown on the membranes for transport studies and the study of cell to cell interaction.

Still another aspect of the invention is a cluster dish having a plurality of wells containing the tissue culture device as described above.

It is an object of this invention to provide a tissue or cell culture device capable of being placed in a cluster dish such that nutrients are provided to tissues or cells while allowing access to the wells in the cluster dish for the addition or removal of media.

Another object of this invention is to provide a device capable of allowing nutrients to pass to the tissues or cells in a manner which approximates the way in which nutrients pass to the cells or tissues within the human body, e.g. which allows the surfaces of the cells attached to a growth surface to receive nutrients via that growth surface.

It is a further object of this invention to provide a tissue or cell culture device capable of supporting cell growth on either side of a growth support in a manner which allows cells on either side of the growth support to communicate by way of soluble factors.

It is an object of this invention to provide a tissue or cell culture device capable of supporting growth on either side of a growth support in a manner which allows cells on either side of the growth support to communicate by way of cell processes which penetrate the growth support.

Yet another object of this invention is to provide a process for studying communication between cells or tissue cultured on either side of a growth support.

Another object of this invention is to provide a transwell with a growth surface that is easily detachable from the transwell.

It is a further object of this invention to provide a transwell with a growth surface that is easily detachable and which growth surface can be placed in a first device in one orientation, removed from the first device and placed in a second device in an inverted orientation.

It is another object of this invention to provide a cell or tissue culture device having a retention element which can be removed and placed in a flow device.

It is yet another object of the present invention to provide a device having two spaced apart membranes forming a chamber for growing cells or tissues.

It is yet another object of this invention to provide a device capable of spacing the side wall of a retention element a sufficient distance apart from the side wall of a well in a cluster dish thereby preventing wicking of fluid between the respective side wall via capillary action.

It is yet another object of this invention to provide a cell or tissue device capable of growing cells in suspension.

BRIEF DESCRIPTION OF THE FIGURES

FIG. 1 is an exploded view of a culture device according to the invention employing a friction fit;

FIG. 2 is a cross-sectional view of the device of FIG. 1, assembled;

FIG. 3 is an exploded view of another culture device of the invention employing a hang fit;

FIG. 4 is a cross-sectional view of the device of FIG. 3, assembled.

FIG. 5b is a cross-sectional view of a second unit for mating with the first unit of the flow device of FIG. 5a;

PREFERRED EMBODIMENTS

Figure 5A:
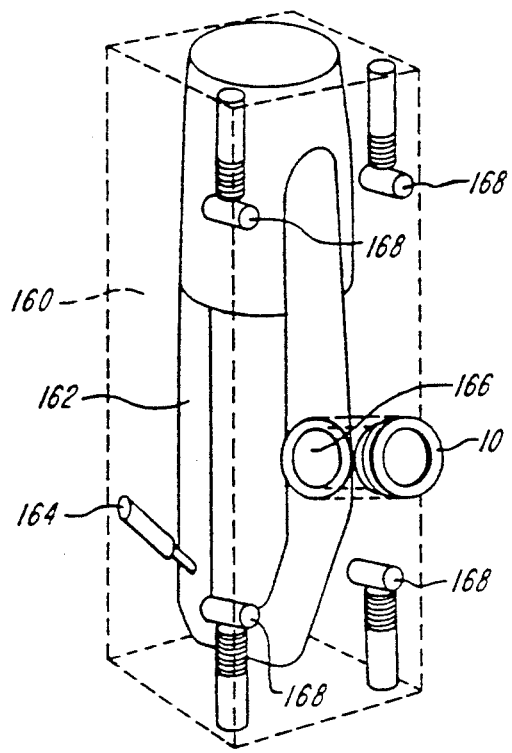
FIG. 5a is a perspective view of a first unit of a flow device for use with the retention element of the invention.

The tissue or cell growth devices shown in each of FIGS. 1 and 2 have a cell or tissue retention element 10 and a hanger 12. The retention element 10 is for supporting the biological sample, e.g. cells or tissues, such that nutrients can be provided to the sample in a manner corresponding or similar to that in vivo. The hanger 12 is constructed and arranged so that it may be suspended from the rim of a culture well 14 of a cluster dish 16, and is for supporting and positioning the retention element within the well 14. The retention element 10 is detachably secured to the hanger 12 so as to allow, among other things, easy manipulation of the retention element 10 separate from the larger, more cumbersome hanger 12.

The cluster dish 16 is only partially illustrated in the drawings, but is shown in detail in U.S. Pat. No. 4,495,289, dated Jan. 2, 1985 and assigned to Data Packaging Corporation, the assignee of the present invention. A disclosure of that patent application is incorporated herein by reference. In the present application, only one well 14 of the cluster dish is shown, and it is to be appreciated that the cluster dish may have six, twelve, twenty four or some other number of wells selected for the particular purpose for which the apparatus is used. Of course, each of the wells of the dish may contain a separate tissue or cell growth device assembly. As each of the other wells are identical to the well shown, and each is used independently of the other, only a single well is illustrated.

The cluster dish has a number of wells 14 each closed at the bottom and open at the top end. The side wall 18 of each well 14 is generally cylindrical and may include a slight draft which facilitates removal of the base from the mold in which it is formed. The cluster dish 16 typically is transparent and may be molded of polystyrene.

A lid (not shown) which may be molded of the same material as the cluster dish 16 is typically provided for positioning on the cluster dish to cover the open end of the wells 14.

While in the foregoing paragraphs, the details of the cluster dish illustrated ar set forth in some detail, it is to be appreciated that the details of the dish do not form a part of the present invention, and the tissue or cell culture device of the present invention may be constructed in various sizes and shapes to fit with other cluster dishes.

In a first embodiment of the invention, shown in FIGS. 1 and 2, the retention element 10 is detachably secured to the hanger 12 by a friction fit. To accomplish this, the retention element 10 and hanger 12 have mating, telescoping portions. These mating, telescoping portions engage one another to form a leak proof fit between the retention element 10 and hanger 12. In this manner, an internal tissue growth chamber 19 defined by the bottom of the hanger 12 and the retention element 10 is formed when the device is assembled.

The hanger member 12 is generally funnel-shaped having a wider, conical top portion and a narrower, substantially cylindrical, bottom portion. The top portion is circumscribed by a radially-extending peripheral flange 20. This flange 20 is constructed and arranged such that it may engage the top peripheral surface 22 of the well 14. The cylindrical bottom portion 24 of the hanger 12 is configured for attachment to the retention element 10. The flange 20 and the bottom portion 24 are joined by conical side wall 26 which decrease in diameter from top to bottom thereby spacing the bottom portion 24 of the hanger 12 from the side wall 18 of the well 14. This arrangement aids in preventing the wicking of fluid between the side wall 16 of the well 14 and side wall 26 of the hanger 12, thereby preventing fluid from wicking either out of the well 14 or into the central, isolated tissue growth chamber 19.

The flange 20 extending about the top periphery of the hanger 12 is annular and preferably is stepped, thereby providing a tight fit between the hanger 12 and the well 14 with little play. The hanger thereby is precisely positioned within the well and is not free to move laterally within the well. The downwardly facing surface of the flange 20 is defined along its outermost edge by a hanger wall 28 which has an outside diameter exceeding the inside diameter of the opening of the well 14, such that it rests on the top peripheral surface 22 of the well 14. Extending downwardly and substantially perpendicular to the hanger wall 28 is annular step wall 30. The outer diameter of step wall 30 is slightly less than the inner diameter of the side wall 18 defining the well 14. This arrangement precisely positions the hanger centrally within the well 14 and prevents lateral movement of the hanger 12 with respect to the well 14.

It should be understood that the step wall 30 need not be continuous. Thus, the step wall can be intermittent. Likewise, other structures are possible. For example, intermittent projections arranged about the periphery of the hanger for engagement with the side wall of the well may accomplish the same purposes, that is, positioning of the hanger centrally within the well and prevention of lateral movement of the hanger within the well.

The flange 20 can extend about the entire periphery of the hanger 12, or preferably may extend about only a portion of the periphery, e.g. about two thirds, thereby providing a flange opening 32 for direct access to the well 14 from a direction substantially perpendicular to the floor of the well 14. Without this opening in the flange, the flange would obstruct such perpendicularly oriented access.

The upwardly facing surface of the flange 20 preferably includes a plurality of spaced knobs 33 that are intended to engage the bottom surface of the top wall of the lid, so as to allow communication between the interior of the well 14 and atmospheric conditions. The spaced knobs 33 also provide for a more controlled evaporation rate of the fluid within the well. In addition, the spaced knobs provide a gap such that when condensation occurs on the underside of the cover, the surface tension of the liquid does not make the hanger stick to the cover when the cover is removed.

Preferably, the flange 20 extends radially inwardly toward the center of the well, and the hanger side wall 26 extend from the flange 20 at a location spaced from the side wall 16 of the well to space the hanger side wall 26 from the well side wall 16. In the preferred embodiment, a downwardly facing spacer wall 34 of the flange 20 extends inwardly from the step wall 30, and the hanger side wall 26 extend from the inner edge of this downwardly facing spacer wall 34.

The hanger side wall 26 preferably include side wall openings 36 which further provide access to the bottom of the well 14, for example via a pipette, without removing the hanger 12 from the well 14. The side wall openings 36 preferably are arranged symmetrically about the hanger side wall. These side wall openings 36 supplement and even may be co-extensive with the flange opening 32 as at combined opening 38 to provide enhanced access to the bottom of the well.

The hanger 12 may include fins 40 which aid in positioning or centering the hanger 12 within the well 14. The fins 40 extend from the step wall 30 downwardly along a portion of the outside surface of hanger side wall 26, terminating prior to the cylindrical bottom portion of the hanger. The fins 40 may abut against the top peripheral surface 22 of the well 14, and may act as a guide in placing and centering the hanger within the well 14. The fins 40 are relatively thin so that they do not provide an adequate surface for wicking.

The bottom of the hanger side walls 26 adjoin the substantially cylindrical bottom portion 24 of the hanger 12. The bottom portion 24 is adapted for a friction fit with the retention element 10. The friction fit is a non leak fit which allows a sample 42 of tissue or cells placed within the tissue growth chamber 19 created by the hanger 12 and the retention element 10 to be isolated from direct contact with the medium 44 in the well. The hollow, cylindrical bottom portion 24 can be open, or may be covered with a membrane as will be described in further detail below.

The hanger 12 can have an annular shoulder stop 46 located on the cylindrical bottom portion 24 close to the junction of the hanger side wall 26 and bottom portion 24. The shoulder stop 46 restricts the telescoping engagement between the retention element 10 and the bottom portion 24 of the hanger 12 and provides an indication when a secure, leak-proof friction fit is achieved. It also provides standardization of the positioning of the retention element 10 on the hanger 12 from device to device.

The retention element 10 of FIGS. 1 and 2 has a hollow, cylindrical side wall 48 defining an annular bottom surface 50. Attached to the annular surface 50 is a tissue growth membrane 52. The tissue growth membrane 52 may be formed of any material capable of supporting cells or tissues substantially isolated from direct contact with medium in the well, while allowing at least selected material to pass through and contact the cells. Such materials include porous inert film, hydrated gels, or layered combinations such as a gel supported upon a screen. Typically, the growth membrane 52 is a porous, track-etched membrane and is attached to the annular surface 50 by heat sealing, solvent bonding, or any other method which does not detrimentally affect the properties of the membrane or the growth of cells upon the membrane.

Preferably, the retention element 10 has a gripping flange 54 extending about the periphery of the top of the side wall 48. This flange 54 provides a grip to facilitate handling the retention element. It also facilitates use of the retention element 10 separate from the hanger 12, such as with a flow device similar to that described in greater detail below, by providing a sealing surface for an O-ring.

In use, a cell or tissue sample 42 is placed on the upwardly facing surface of the growth membrane 52. Medium is added to the well 14 to a level such that the medium contacts the downwardly facing surface of the growth membrane 52, but less than that amount that would cause the medium to overflow the side wall openings 36 and contact the upwardly facing surface of the growth membrane 52 directly. Depending upon the particular test or experiment being conducted, the same or a different medium may be added to the open growth chamber 19, in direct contact with the cell or tissue sample 42. Likewise, the open growth chamber 19 may be substantially free of medium. Test materials optionally may be added either to the medium in the well 14 or the medium in the growth chamber 19. The medium in the well, as well as test materials in the well, contact the cell or tissue sample only by diffusion through the growth membrane 52.

The medium in the well may be changed or maintained without removal of the hanger from the well. After sufficient culture, the cell or tissue sample 42 may be examined or manipulated by removing the device from the well 14 and detaching the retention element 10 from the hanger 12.

It will be appreciated that when the culture device is positioned within the well, a lid would serve to hold the culture device in position within the well. Consequently, the assembly will not float in the solution and cause the stepped flange to become unseated. While it is customary to position the growth membrane 52 approximately one millimeter above the bottom wall 56 of the well, if desired, additional space between the growth membrane 52 and the bottom wall 56 of the well 14 may be provided either by adjusting the size of the hanger or by selecting a well having a greater depth.

In another embodiment of the invention, the retention element is hung from the hanger preferably as shown in FIGS. 3 and 4. In this embodiment, the hanger 112 and the retention element 110 are formed substantially as telescoping, right, hollow cylinders, with the retention element 110 sized to be positioned within the hollow of the hanger 112.

The hanger 112 of this embodiment has a stepped flange 114 substantially the same as that described in connection with the embodiment of FIGS. 1 and 2. This flange includes a hanger wall 116 for engagement with the top peripheral surface 118 of the well 14, and a step wall 120 for positioning the hanger within the well 14 and for preventing lateral movement of the hanger within the well. The stepped flange 114 also includes a spacer wall 122 to which the cylindrical hanger side wall 124 are attached. The cylindrical hanger side wall 124 extends downwardly from the inner edge of the spacer wall 122 of the flange and thus are spaced from the side wall of the well 14.

The hanger side wall 124 is substantially cylindrical. Spaced evenly about only the top portion of the hanger side wall 124 are openings 126. These openings 126 are substantially rectangular in shape and extend preferably at least part way into the spacer wall 122 of the flange 114, thereby providing for access to the medium within the well 14. It will be readily understood that these openings could extend completely through the stepped flange as shown in FIGS. 1 and 2.

Each opening 126 is defined in part by three walls, two side walls 128 extending substantially parallel with respect to one another and substantially downwardly along the hanger side wall 124, and a bottom wall 130 connecting the two side wall 128. The bottom walls 130 act as a seat for interengagement with protrusions on the retention element 110 such that the retention element 110 may be fitted within and suspended from the hanger side walls 124 of the hanger 112.

The hanger 112 also can have fins 132 and knobs 133 which are constructed and arranged substantially as described in connection with FIGS. 1 and 2.

The bottom end of the cylindrical hanger side wall 124 defines a bottom annular edge 134. A membrane 136 may be attached to this edge to define a cup-like hanger. In this instance, the interior space defined by the cup-like hanger would be isolated from the medium within the well (FIG. 4). Alternatively, no membrane is attached to the bottom edge 134 of the hanger 112, and the interior space defined by the hanger side wall 124 in this instance would not be isolated from the medium within the well.

The retention element 110 also is substantially cylindrical and is sized and shaped to fit substantially within the interior of the hanger 112. Protrusions 138 are located toward the top of the exterior surface of the retention element 110, projecting outwardly. The protrusions 138 are constructed and arranged so as to interengage with the bottom wall 130 of openings 126 such that the retention element 110 may be hung from the hanger 112. The protrusions 138 are much like the peripheral flange 114 described above. The protrusions include a protrusion hanger wall 140 for engagement with the bottom wall 130 of the openings 126. A protrusion step wall 142 extends downwardly from the inner edge of the protrusion hanger wall 140 and substantially perpendicular to the protrusion hanger wall 140. The protrusion step walls 142 are sized to fit just within the inside surface of the hanger side walls 124, with little play. The retention element 110 thereby is precisely positioned within the hanger and is not free to move laterally within the hanger. A protrusion spacer wall 144 extends laterally inwardly from the protrusion step wall 142. The cylindrical side walls 146 of the retention element 110 extend downwardly from the inner edge of the protrusion spacer wall 144 and are spaced from the hanger side walls 124 by the protrusion spacer wall 144. In the preferred embodiment, the spacer wall 144 extends completely about the top portion of the exterior surface of the side walls 146 of the retention element 110.

The side walls 146 of the retention element 110 terminate in a bottom annular edge 148. A growth membrane 150 is attached to this bottom annular edge 148 as described above in connection with retention element 10.

As illustrated in FIG. 4, the combination of growth membrane 136 on the hanger 112 and growth membrane 150 on the retention element 110 creates a double-membrane chamber 152 between the two membranes. Such an arrangement may be useful in a variety of contexts. For example, a first cell or tissue sample may be placed within the double-membrane chamber 152 and a second cell or tissue sample may be placed on the upwardly facing surface of the growth membrane 150, separated from the first cell or tissue sample by the growth membrane 150. The effect of the releasate of one of the tissue samples on the other of the tissue samples then could be studied. Other applications will be obvious to those of ordinary skill in the art.

Flow devices recently have been devised for studying transcellular transport of drugs and nutrients in cultured cells. A monolayer of cells is cultured upon a porous membrane surface. This monolayer of cells can be placed as a barrier between two flow-channels of circulating medium. Then, a molecule such as a drug, may be introduced into one of the flow channels, and the presence of the drug or of products of cells stimulated by the drug may be measured in the other of the flow channels.

Figure 5B:
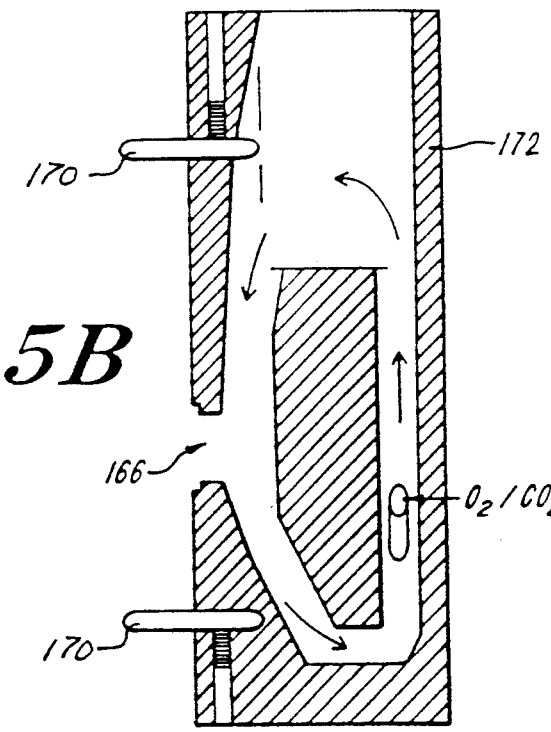

One such flow device is shown in FIG. 5A and 5B. FIG. 5A is a perspective view of one half of the flow cell and FIG. 5B is a cross-sectional view of the other half of the flow cell. The flow cell device has a first unit 160 (FIG. 5A) substantially in the shape of a rectangular block. The first unit 160 includes a substantially U-shaped flow channel 162. An $O_2/CO_2$ inlet 164 is provided through a side wall of the first unit and communicates with one side of the U-shaped flow channel 162. A stepped cylindrical opening extends through an opposite side wall of the first unit 160 and communicates with the other side of the U-shaped flow channel 162. A plurality of pin receiving openings 168 also are located on the same side of the first unit as the stepped cylindrical opening 166.

Figure 6:
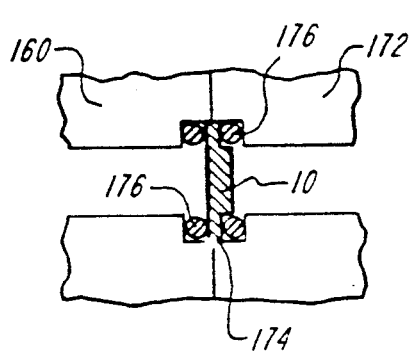
FIG. 6 is a schematic cross-sectional view of the channel formed between the first and second units of FIGS. 5a and 5b when assembled.

The second unit 170 is configured as the mirror image of the first unit 160, except that the second unit carries pins 172 for mating with the openings 168. As will be readily understood, when the first unit and second unit are aligned and brought together in face to face relationship by the mating of the pins 172 with the openings 168, the stepped cylindrical openings 166 mate to form a cylindrical channel with an annular wider portion located centrally of the channel. This annual wider portion may be used to capture the flange of the retention element 10 of the invention. This arrangement is shown schematically in FIG. 6 wherein the retention flange 54 of the retention element 10 is seen sealingly captured between a pair of O-rings 176 within the annular wider portion 174 of the channel. By this arrangement, the media flowing through the U-shaped channel 162 of the first unit 160 may communicate with the media flowing through the U-shaped channel of the second unit 170 only by passing through the cells supported on the surface of the growth membrane of a retention element 10.

This invention also pertains to a device for maintaining cells or tissues including a cluster dish 16 having the tissue or cell growth devices described above placed in each well 14. The cluster dish 16 has a plurality of wells 14 attached to a tray 154 as described in U.S. Pat. No. 4,495,289 issued Jan. 2, 1985, the contents of which are hereby incorporated by reference. The tray 154 of the cluster dish 15 may further include a cover (not shown).

Preferably, all the components are molded from the same material which is a transparent polystyrene. The components are molded using art-recognized techniques.

Figure 7:
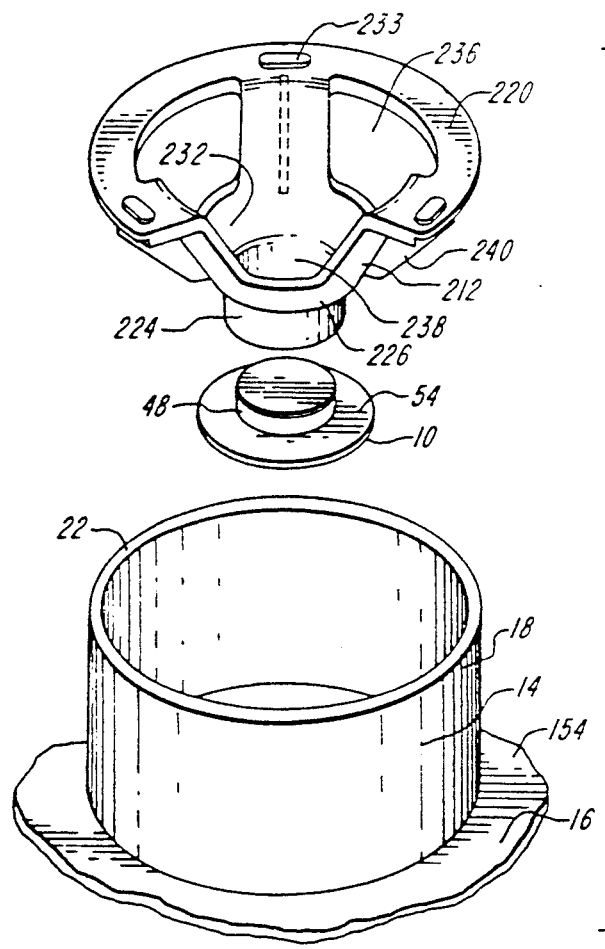
FIG. 7 is an exploded view of another culture device of the invention employing a friction fit and having a growth surface in an inverted orientation compared to that of the embodiment shown in FIG. 1.
Figure 8:
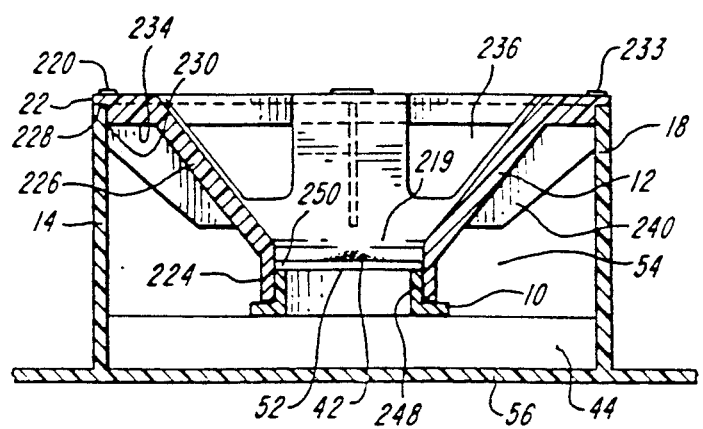
FIG. 8 is a cross-sectional view of the device of FIG. 7, assembled.

In another embodiment of the invention, shown in FIGS. 7 and 8, retention element 10 is detachably secured to hanger 212 by a friction fit. In this embodiment, retention element 10 is substantially identical to that depicted in FIGS. 1 and 2. The principal difference is that the hangers of the two embodiments differ in the width of their cylindrical bottom portions. This difference permits retention element 10 to be secured to hanger 212 in an inverted orientation compared to that shown in FIGS. 1 and 2. To position retention element 10 within hanger 212, retention element 10 and hanger 212 have mating, telescoping portions with the hollow of the telescoping portion of hanger 212 sized to be positioned within the telescoping portion of retention element 10. When retention element 10 and hanger 212 engage one another to form a leak proof fit, an internal tissue growth chamber 219 defined by the bottom portion 224 of hanger 212 and retention element 10 is formed.

The hanger member 212, like the hanger member 12, is generally funnel-shaped having a wider, conical top portion and a narrower, substantially cylindrical, bottom portion. The top portion is circumscribed by a radially-extending peripheral flange 220. This flange 220 is constructed and arranged such that it may engage the top peripheral surface 22 of well 14. Flange 220 and bottom portion 224 are joined by conical side wall 226 which decreases in diameter from top to bottom thereby spacing the bottom portion 224 of the hanger 212 from side wall 18 of well 14.

Flange 220 extending about the top periphery of hanger 212 is annular and preferably is stepped, thereby providing a tight fit between the hanger 212 and the well 14 with little play. The hanger is precisely positioned within the well and is not free to move laterally within the well. The downwardly facing surface of the flange 220 is defined along its outermost edge by a hanger wall 228 which has an outside diameter exceeding the inside diameter of the opening of the well 14, such that it rests on the top peripheral surface 22 of the well 14. Extending downwardly and substantially perpendicular to the hanger wall 228 is annular step wall 230. The outer diameter of step wall 230 is slightly less than the inner diameter of the side wall 218 defining the well 14. This arrangement precisely positions the hanger centrally within the well 14 and prevents lateral movement of the hanger 212 with respect to the well 14.

The flange 220 can extend about the entire periphery of the hanger 212, or preferably may extend about only a portion of the periphery, e.g. about two thirds, thereby providing a flange opening 232 for direct access to the well 14 from a direction substantially perpendicular to the floor of the well 14. Without this opening in the flange, the flange would obstruct such perpendicularly oriented access.

The upwardly facing surface of the flange 220 preferably includes a plurality of spaced knobs 233 that are intended to engage the bottom surface of the top wall of the lid, so as to allow communication between the interior of the well 14 and atmospheric conditions. The spaced knobs 233 also provide for a more controlled evaporation rate of the fluid within the well.

Preferably, the flange 220 extends radially inwardly toward the center of the well, and the hanger side wall 226 extends from the flange 220 at a location spaced from the side wall 18 of the well to space the hanger side wall 226 from the well side wall 18. A downwardly facing spacer wall 234 of the flange 20 extends inwardly from the step wall 230. Hanger side wall 226 extends inwardly and downwardly from the inner edge of downwardly facing spacer wall 234 to bottom portion 224.

The hanger side wall 226 preferably includes side wall openings 236 which further provide access to the bottom of the well 14, for example via a pipette, without removing the hanger 212 from the well 14. The side wall openings 236 preferably are arranged symmetrically about the hanger side wall. These side wall openings 236 supplement and may be co-extensive with the flange opening 232 as at combined opening 238 to provide enhanced access to the bottom of the well.

The hanger 212 may include fins 240 which aid in positioning or centering the hanger 212 within the well 14. The fins 240 extend from the step wall 230 downwardly along a portion of the outside surface of hanger side wall 226, terminating prior to the cylindrical bottom portion of the hanger. The fins 240 may abut against the top peripheral surface 22 of the well 14, and may act as a guide in placing and centering the hanger within the well 14. The fins 240 do not provide an adequate surface for wicking because they are relatively thin.

The bottom of the hanger side walls 226 adjoin the substantially cylindrical bottom portion 224 of the hanger 212. The bottom portion 224 is adapted for a friction fit with the retention element 10. In this embodiment, the friction fit is accomplished with the bottom portion 48 of retention element 10 sized to be positioned within the hollow of bottom portion 224 of hanger 212. The friction fit is a non-leak fit which allows a sample 42 of tissue or cells placed within the tissue-growth chamber 219 created by the hanger 212 and the retention element 10 to be isolated from direct contact with the medium 44 in the well. The hollow, cylindrical bottom portion 224 is open to receive retention element 10.

It should be understood that the variations in hanger shape and wall structure discussed in connection with the embodiment shown in FIGS. 1 and 2 are also applicable to the present embodiment.

The retention element 10 of FIGS. 7 and 8 is identical to that previously described in connection with FIGS. 1 and 2. However, retention element 10 is used in an inverted orientation in the embodiment shown in FIGS. 7 and 8.

In use, a cell or tissue sample 42 can be placed on the upwardly facing surface of growth membrane 52 (FIG. 8). Medium is added to the well 14 to a level such that the medium contacts the growth membrane 52, but preferably less than that amount that would cause the medium to overflow the side wall openings 236. Depending upon the particular test or experiment being conducted, the same or a different medium may be added to the open growth chamber 219, in direct contact with the cell or tissue sample 42. Likewise, the open growth chamber 219 may be substantially free of medium. Test materials optionally may be added either to the medium in the well 14 or the medium in the growth chamber 219. The medium in the well, as well as test materials in the well, contact the cell or tissue sample only by diffusion through the growth membrane 52. The medium in the well may be changed or maintained without removal of the hanger from the well. After sufficient culture, the cell or tissue sample 42 may be examined or manipulated by removing the device from the well 14 and detaching the retention element 10 from the hanger 212.

In one embodiment of the invention, the retention element 10 is used sequentially, first with hanger 212 and then with hanger 12. A monolayer of cells first is grown on the surface of the growth membrane 52 facing upwardly when used with the hanger 212. Initially, there is no vapor lock beneath the membrane because the monolayer has not yet formed and air captured within the side walls 48 of the retention element can escape through the membrane. After the monolayer has formed, then the retention element 10 is removed from the hanger 212, inverted and then friction fit onto the hanger 12. The monolayer of cells now faces downwardly and a second cell layer is grown onto the opposite and now upwardly facing surface of membrane 52. In this manner, the same or different types of cells or tissues, may be cultured on each side of the growth membrane. It should be understood that if a monolayer is first grown onto the membrane when the device is used with hanger 12, then the likelihood of creating a vapor lock when the device is inverted and used with hanger 212 is greatly enhanced.

The foregoing arrangement permits the detection and study of communication between cells located on either side of the growth surface, as mediated by soluble factors released from the cultured cells or tissue. Further, if the growth membrane has a fairly large pore size, cell processes may penetrate the membrane, thereby permitting the study of communication between cells located on either side of the growth surface, as mediated by cellular processes growing through the growth support and permitting cell cell contact.

In addition to the two cell types growing on each side of growth membrane 52, a third cell type may be cultured in well 14 in accordance with standard culturing procedures. In this manner, cellular communication as mediated by soluble factors in a three cell system may be studied.

Figure 9:
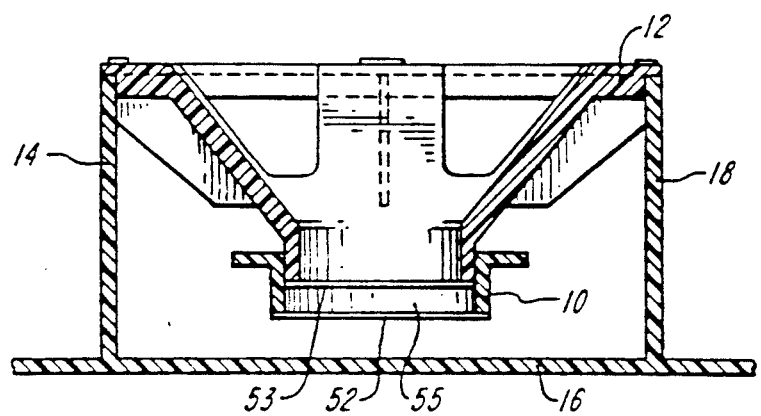
FIG. 9 is a cross-sectional view of the hanger and retention element of FIG. 1, further including a membrane attached directly to the hanger.

As illustrated in FIG. 9, a growth membrane 53 may be secured to hanger 12. The combination of growth membrane 53 on hanger 12 and growth membrane 52 on retention element 10 creates a double-membrane chamber 55 between the two membranes. FIG. 9 is not extensively labeled in order to more clearly illustrate double-membrane chamber 55. However, the component structures of hanger 12 and of retention element 10 are identical to those shown in FIGS. 1 and 2. Such an arrangement may be useful in variety of contexts as described above in connection with FIGS. 3 and 4. Other applications will be obvious to those of ordinary skill in the art.

Having described this invention in detail, those skilled in the art will appreciate that numerous modifications can be made thereof without departing from its spirit. Therefore, it is not intended to limit the breadth of the invention to the embodiments illustrated and described. Rather, the scope of this invention is to be determined by the appended claims and their equivalents.

What is claimed is:

1. A process for growing cells or tissue on two sides of a growth support comprising:
   (a) providing a culture device comprising a retention element and a first hanger detachably secured thereto, said retention element including a growth surface having a first side and a second side, wherein the retention element has a first mating telescoping portion and a second mating telescoping portion, wherein said first hanger has a mating telescoping portion to detachably secure the retention element to the first hanger by a friction fit formed by engagement of the retention element first mating telescoping portion and said first hanger telescoping portion;
   (b) placing the culture device in a nutrient-containing culture well so as to permit culturing cells or tissue on the first side of the growth support;
   (c) detaching the retention element from said first hanger;
   (d) inverting the retention element and attaching it to a second hanger, wherein the second hanger has a mating telescoping portion to detachably secure the retention element to the second hanger by a friction fit formed by engagement of the second telescoping portion of the retention element and the mating telescoping portion of the second hanger; and
   (e) placing the culture device in the nutrient-containing culture well so as to permit culturing cells or tissue on the second side of the growth support.

2. The process for growing cells or tissue as claimed in claim 1 wherein the hangers and the retention element are constructed and arranged such that the friction fit provides a leak proof junction.

3. A tissue or cell growth device for placement within a culture well comprising:
   a hanger having side walls and a bottom portion, said hanger constructed and arranged to be supported within a culture well having well side walls and a well bottom such that said hanger side walls and bottom portion do not touch the well side walls or well bottom, and
   a retention element including a side wall having an annular bottom surface and a growth surface attached thereto, the retention element detachably secured to the bottom portion of the hanger whereby said retention element is suspended horizontally within the well at a preselected location within
   wherein the retention element and the hanger have mating telescoping portions to detachably secure the retention element to the hanger by a friction fit formed by engagement of the telescoping portions, and wherein the mating telescoping portion of the retention element fits over the mating telescoping portion of the hanger.

4. A tissue or cell growth device for placement within a culture well comprising:
  a hanger having side walls and a bottom portion, said hanger constructed and arranged to be supported within a culture well having well side walls and a well bottom such that said hanger side walls and bottom portion do not touch the well side walls or well bottom, and
  a retention element including a side wall having an annular bottom surface and a growth surface attached thereto, the retention element detachably secured to the bottom portion of the hanger whereby said retention element is suspended horizontally within the well at a preselected location within the well,
  wherein the retention element and the hanger have mating telescoping portions to detachably secure the retention element to the hanger by a friction fit formed by engagement of the telescoping portions, and wherein the mating telescoping portion of the hanger fits over the mating telescoping portion of the retention element.

5. A tissue or cell growth device as claimed in claim 3 or 4 wherein the hanger includes a substantially hollow cylindrical portion and a peripheral flange, the flange constructed and arranged to engage top and inner peripheral surfaces of the well in a manner such that the cylindrical portion is positioned within but not touching the side walls or bottom of the well.

6. A tissue or cell growth device as claimed in claim 5 wherein the peripheral flange includes openings for providing access to the bottom of the well when the device is supported within the well by the peripheral flange.

7. A tissue or cell growth device as claimed in claim 3 or 4 wherein the hanger has a peripheral flange constructed and arranged to engage top and inner peripheral surfaces of the well, and has hollow, substantially cylindrical side walls attached to and extending from the flange.

8. A tissue or cell growth device as claimed in claim 7 wherein the peripheral flange includes openings for providing access to the bottom of the well when the device is supported within the well by the peripheral flange.

9. A tissue or cell growth device as claimed in claim 3 or 4 wherein the hanger includes a flange constructed and arranged to engage a peripheral surface of the well, and also includes conical side-walls of decreasing diameter attached to and extending from the flange.

10. A tissue or cell growth device as claimed in claim 9 wherein the peripheral flange includes openings for providing access to the bottom of the well when the device is supported within the well by the peripheral flange.

11. A tissue or cell growth device as claimed in claim 3 or 4 wherein the hanger and retention element are constructed and arranged such that the friction fit provides a leak proof junction.

* * * * *